(12) United States Patent
Mulac et al.

(10) Patent No.: US 7,338,442 B2
(45) Date of Patent: Mar. 4, 2008

(54) CRANK RETRACTOR HANDLE

(75) Inventors: Anthony J. Mulac, East Jordan, MI (US); Daniel K. Farley, Traverse City, MI (US)

(73) Assignee: Peak Performance Company, Traverse City, MI (US)

( * ) Notice: Subject to any disclaimer, the term of this patent is extended or adjusted under 35 U.S.C. 154(b) by 668 days.

(21) Appl. No.: 10/405,277

(22) Filed: Apr. 2, 2003

(65) Prior Publication Data
US 2004/0199055 A1    Oct. 7, 2004

(51) Int. Cl.
  A61B 1/32    (2006.01)
(52) U.S. Cl. .................................... 600/226
(58) Field of Classification Search ............... 403/105, 403/344, 389, 391; 248/122.1, 124.1, 124.2, 248/125.1, 125.3, 125.7–125.9, 214, 226.11, 248/227.4, 276.1, 277.1, 278.1, 279.1, 281.11; 600/201, 206
See application file for complete search history.

(56) References Cited

U.S. PATENT DOCUMENTS

| | | | | |
|---|---|---|---|---|
| 3,221,743 | A | * 12/1965 | Thompson et al. | ............ 606/1 |
| 4,254,763 | A | 3/1981 | McCready et al. | |
| 4,424,724 | A | * 1/1984 | Bookwalter et al. | .......... 74/540 |
| 4,497,092 | A | * 2/1985 | Hoshino | ........................ 24/514 |
| 4,617,916 | A | * 10/1986 | LeVahn et al. | ............. 600/228 |
| 4,718,151 | A | 1/1988 | LeVahn et al. | |
| 4,971,038 | A | 11/1990 | Farley | |
| 5,020,195 | A | 6/1991 | LeVahn | |
| 5,025,780 | A | 6/1991 | Farley | |
| 5,375,481 | A | * 12/1994 | Cabrera et al. | .......... 74/577 M |
| 5,393,161 | A | * 2/1995 | Mata et al. | .................. 403/133 |
| 5,727,899 | A | 3/1998 | Dobrovolny | |
| 5,788,630 | A | * 8/1998 | Furnish | ....................... 600/232 |
| 5,792,046 | A | 8/1998 | Dobrovolny | |
| 5,888,197 | A | 3/1999 | Mulac et al. | |
| 5,897,087 | A | 4/1999 | Farley | |
| 5,984,865 | A | 11/1999 | Farley et al. | |
| 6,017,008 | A | 1/2000 | Farley | |
| 6,264,396 | B1 | * 7/2001 | Dobrovolny | ................. 403/391 |
| 6,312,184 | B1 | * 11/2001 | Hoshino | ...................... 403/104 |
| 6,602,190 | B2 | * 8/2003 | Dobrovolny | ................ 600/234 |
| 6,729,205 | B2 | * 5/2004 | Phillips | .................... 74/577 M |
| 6,949,105 | B2 | * 9/2005 | Bryan et al. | ................. 606/130 |
| 7,125,380 | B2 | * 10/2006 | Yager | .......................... 600/227 |

* cited by examiner

*Primary Examiner*—Anuradha Ramana
(74) *Attorney, Agent, or Firm*—McAndrews, Held & Malloy, Ltd.

(57) ABSTRACT

The present invention relates to an apparatus for adapting a non-cylindrical serrated surgical retractor blade handle to the cylindrical bore of a universal joint. The apparatus includes an adaptor housing having a retractor handle passageway, at least a portion of the retractor handle passageway being configured to receive the slideable insertion of a non-cylindrical retractor blade handle. The adaptor housing is configured for rotational insertion into the cylindrical bore of a clamping member, thereby allowing the adaptor housing, the non-cylindrical retractor blade handle, and an attached retractor blade, to rotate about the longitudinal axis of the non-cylindrical retractor blade handle. In the illustrated embodiment, a pawl mechanism is connected to the adaptor housing and configured for automatic engagement with at least one of a plurality of serrations that are located on the non-cylindrical retractor blade handle, thereby allowing for the efficient adjustment and automatic locking of the linear position of the non-cylindrical retractor blade handle relative to the operative site.

8 Claims, 4 Drawing Sheets

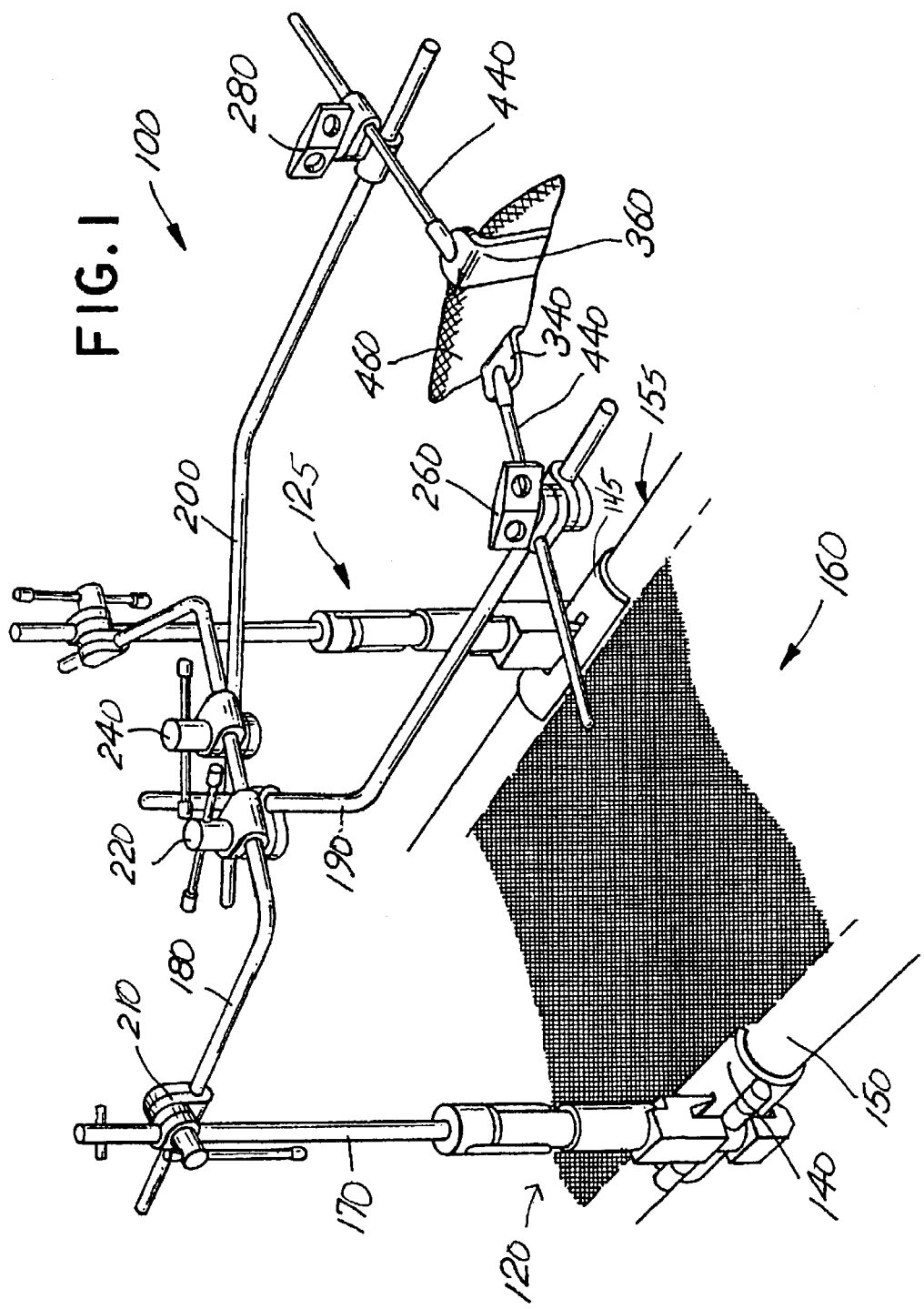

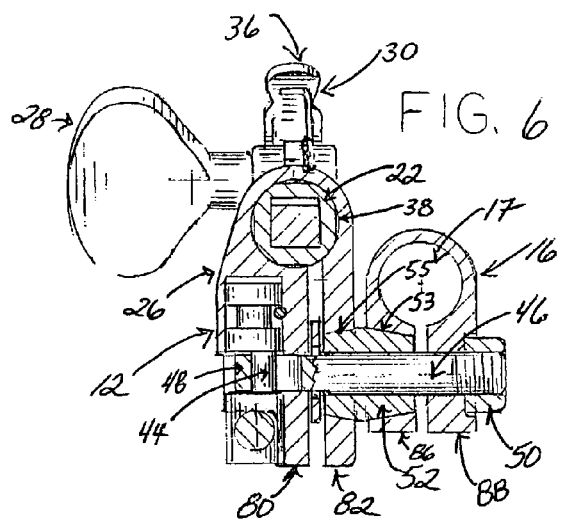
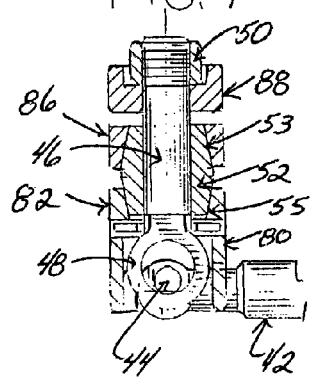
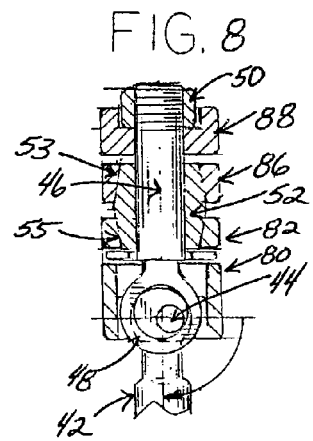
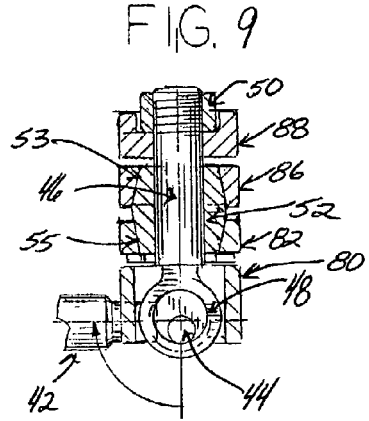
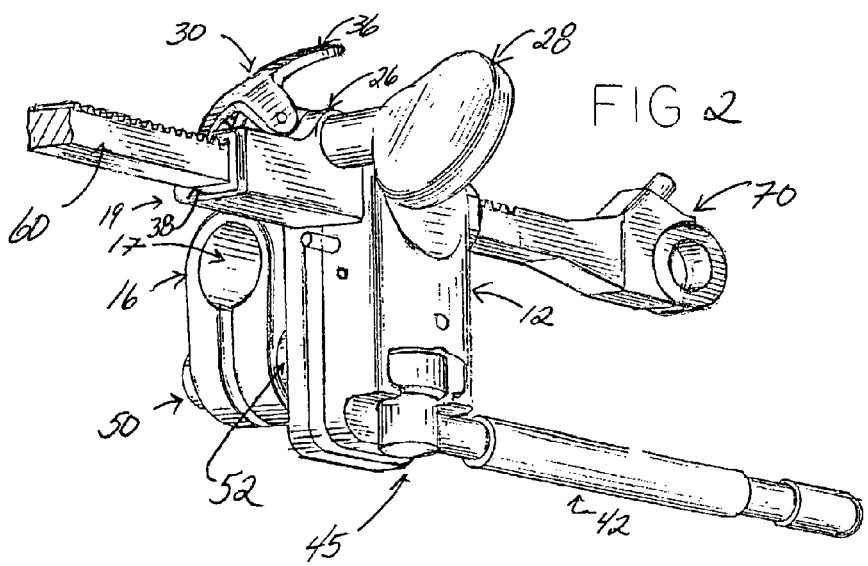

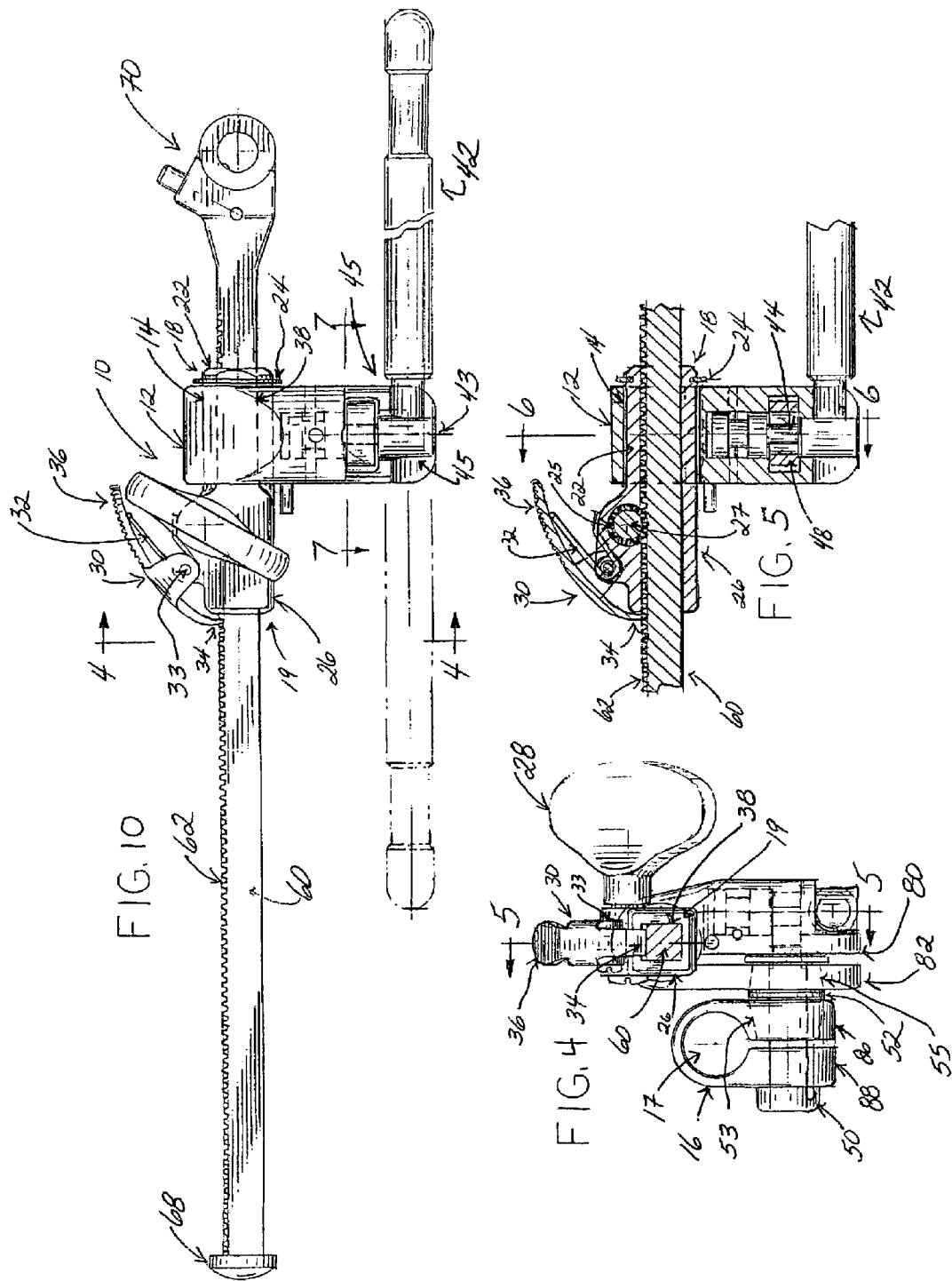

CRANK RETRACTOR HANDLE

BACKGROUND OF THE INVENTION

The present invention pertains to surgical retractor systems. More particularly, the present invention relates to an apparatus for adapting a non-cylindrical serrated surgical retractor blade handle to a universal joint, and, more particularly, an adaptor that provides the ability to rotate a non-cylindrical retractor blade handle within a universal joint clamping apparatus. The present invention provides surgeons with the ability to precisely position retractor blades, while also providing a ratchet engagement for efficient adjustment and automatic locking of the linear position of a non-cylindrical retractor blade handle and associated retractor blade.

In surgical operations, it is customary to use a retraction device in order to properly access internal organs and bone structures. Such devices are particularly designed to hold back a patient's anatomy in the immediate area of the operative site, thereby enabling a surgeon to have both an optimal view of the operative site and a sufficiently opened area within which to work.

In the past, various measures have been employed to improve the ease and efficiency of positioning and/or readjusting the location of retractor blades, while also maintaining a sterile operating environment. Surgical retraction devices have utilized universal joints that allow a first clamping member, which clamps a retractor blade handle, to rotate along the same axis as a second clamping member, which typically clamps onto a retractor system frame. Such systems allow surgeons to swivel and/or rotate the position of the retractor blade handle so that the retractor blade may be placed at a desired position relative to the operative site. Examples of such devices are disclosed in U.S. Pat. Nos. 3,221,743, 4,617,916, 5,025,780, and 5,888,197.

Other retractor systems, such as U.S. Pat. No. 4,254,763, attach retractor blades to square or rectangular serrated retractor blade handles. These square or rectangular serrated retractor blade handles are inserted into a clamping apparatus, which include a quick release pawl mechanism, and which is typically securely affixed to the retractor system frame. The combination of the square or rectangular serrated retractor blade handle and the quick-release pawl mechanism creates a traditional ratchet engagement. This ratchet engagement automatically locks the non-cylindrical retractor blade handle in position, thereby eliminating the time and effort normally associated with manually tightening the retractor blade handle at its desired position. Furthermore, the ratchet action allows for quick and easy adjustment of the linear position of the square or rectangular serrated retractor blade handle relative to the pawl mechanism.

In order to mate square or rectangular serrated retractor blade handles, prior art devices require that the clamping apparatus have an orifice that also has square or rectangular configuration so that clamping apparatus is able to receive the slideable insertion of the retractor blade handle. Unfortunately, unlike cylindrical retractor blade handles, the square or rectangular configurations of the retractor blade handle and mating orifice render the retractor blade handle incapable of rotation within the clamping apparatus. The inability to rotate a retractor blade handle within a clamping apparatus hinders a surgeon's ability to adjust the angular position of the retractor blade relative to the operative site.

U.S. Pat. No. 6,017,008 teaches a clamping apparatus that incorporates both a second clamping member and a first clamping member, the first clamping member having a quick release pawl mechanism and a square traverse bore that is configured to receive the slideable insertion of a non-cylindrical retractor blade handle. However, as mentioned above, the square cross section of the traverse bore prohibits the rotation of the non-cylindrical retractor blade handle, and attached retractor blade, about the longitudinal axis of the non-cylindrical retractor blade handle.

It is therefore an object of this invention to provide an apparatus that permits the rotation of a non-cylindrical retractor blade handle within a clamping apparatus and about the longitudinal axis of the non-cylindrical retractor blade handle.

It is a further object of this invention to provide an adaptor for a non-cylindrical retractor blade handle that permits the rotational adjustment of the non-cylindrical retractor blade handle independent of the rotational position of the second clamping member.

A further object of this invention is to provide a clamping apparatus that permits quick and easy adjustment and automatic tightening of the linear position of a non-cylindrical retractor blade handle.

These and other desirable characteristics of the present invention will become apparent in view of the present specification, including the claims and drawings.

SUMMARY OF THE INVENTION

The present invention is directed to an apparatus that adapts non-cylindrical retractor blade handles to a universal joint. More particularly, the present invention relates to an apparatus that adapts non-cylindrical retractor blade handles to a universal joint, and which also permits the rotational adjustment of the non-cylindrical retractor blade handle, and attached retractor blade, about the longitudinal axis of the non-cylindrical retractor blade handle.

The apparatus includes an adapter housing having a retractor handle passageway, the retractor handle passageway being configured to both receive the slideable insertion of the non-cylindrical retractor blade handle, and to prevent the rotation of the non-cylindrical retractor blade handle relative to the adaptor housing. At least a portion of the adaptor housing is configured for rotatable insertion into the clamping bore of the universal joint, thereby permitting the rotation of both the adaptor housing and non-cylindrical retractor blade handle, and attached retractor blade, about the longitudinal axis of the non-cylindrical retractor blade handle.

In one embodiment, a pinion is operably connected to the adapter housing. The pinion is configured for engagement with at least one of a plurality of serrations on the non-cylindrical retractor blade handle, thereby aiding in the linear positioning of the non-cylindrical retractor blade handle. A pawl mechanism is operably connected to the adaptor housing for engagement with at least one of the plurality of serrations on the non-cylindrical retractor blade handle, thereby allowing for the rapid adjustment and automatic locking of the linear position of the non-cylindrical retractor blade handle.

A locking mechanism connects the first and second clamping members of the universal joint. The locking mechanism secures the rotational positions of the second and first clamping members, the adaptor housing, and the non-cylindrical retractor blade handle. However, the locking mechanism does not prohibit the adjustment of the linear position of the non-cylindrical retractor blade handle, and attached retractor blade. Therefore, the apparatus provides surgeons with the ability to efficiently and precisely position, and adjust, the linear location of a retractor blade during an operation without unlocking the locking mechanism, and without having to manually tighten the non-cylindrical retractor blade handle at the desired location, while still continuing to maintain a sterile operating environment.

BRIEF DESCRIPTION OF THE DRAWINGS

For a more complete understanding of this invention reference should now be had to the embodiment illustrated in greater detail in the accompanying drawings and described below by way of example of the invention.

FIG. 1 illustrates the use of a conventional surgical retraction system.

FIG. 2 is a perspective view of an embodiment of the crank universal joint.

FIG. 4 is a partial cross sectional view of the rear side of an embodiment of the crank universal joint.

FIG. 5 is a cross-sectional view of the cam side of an embodiment of the crank universal joint.

FIG. 6 is a cross-sectional view of the front portion of an embodiment of the crank universal joint.

FIGS. 7, 8, and 9 are cross sectional views depicting the operation of the locking mechanism of an embodiment of the invention.

FIG. 10 is a partial cross-sectional view of the cam side of an embodiment of the invention.

DETAILED DESCRIPTION OF THE ILLUSTRATED EMBODIMENT

Figure 3:
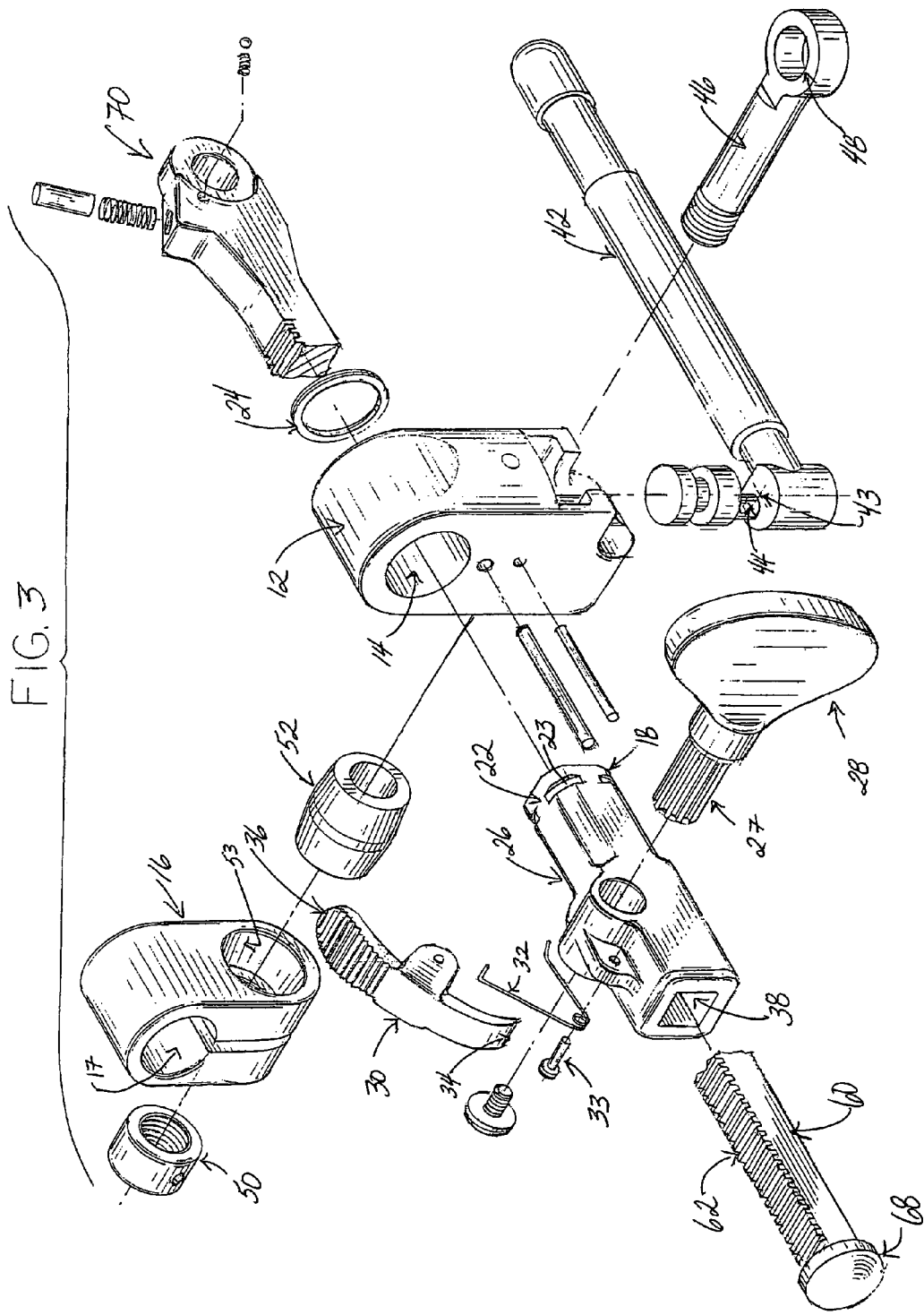
FIG. 3 is an exploded perspective view of an embodiment of the crank universal joint.

FIG. 1 illustrates the use of conventional universal joints in a surgical retraction system 100. Adjustable clamps 120, 125 are secured, through the use of adapters 140, 145, to the frames 150, 155 of a conventional framed stretcher or surgical table 160. A post 170 extends vertically from a clamp 120 to provide support for a cross bar 180, which in turn provides support for a pair of extension arms 190, 200. The crossbar 180 is secured to the post 170 by a multidirectional joint clamp 210. The extension arms 190, 200 are secured to the cross bar 180 by a pair of multidirectional joint clamps 220, 240. Additional joint clamps 260, 280 are disposed along the extension arms 190, 200 for rigidly securing any number of retractor blades 340, 360 to the extension arms 190, 200.

The joint clamps 260, 280 allow for both the rotation of the clamping mechanism along the longitudinal axis of the extension arms 190, 200 and the pivotable placement of the retractor blade handle 440 in relation to the extension arms 190, 200. The surgeon is then able to place the retractor blades 340, 360 at their desired position in the incised opening 460 made by the surgeon. The retractor blades 340, 360 are then used to retract the patient's anatomy, thereby making the incised opening 460 accessible to the surgeon.

FIG. 2 illustrates a perspective view of the illustrated embodiment of the crank universal joint 10. The crank universal joint 10 is shown as including a non-cylindrical retractor blade handle 60 having a plurality of serrations 62, an adapter housing 26, a first clamping member 12, a second clamping member 16, and a locking mechanism 45. The non-cylindrical serrated handle 60, is shown as being inserted into the retractor handle passageway 38 of the adaptor housing 26. A pawl mechanism 30 is both operably attached to the adaptor housing 26 and engaging at least one of the plurality of serrations 62.

FIG. 3 illustrates an exploded perspective view of the illustrated embodiment of the crank universal joint 10. The adapter housing 26 is shown as having a sleeve 22 and a retractor handle passageway 38. The retractor handle passageway 38 is configured to receive the slideable insertion of a non-cylindrical retractor blade handle 60 into the adapter housing 26. The retractor handle passageway 38 may have a non-cylindrical configuration that is substantially similar to the configuration of the non-cylindrical retractor blade handle 60. Additionally, at least a portion of the retractor handle passageway 38 may be a cylindrical orifice so as to reduce the time and expense associated with manufacturing a non-cylindrical passageway throughout the entire length of the adaptor housing 26.

The sleeve 22 is configured for rotational insertion into the clamping bore 14 of the first clamping member 12, as shown in FIGS. 2, 5, and 6. The rotational insertion of the sleeve 22 into the clamping bore 14 allows for the rotational movement of the adaptor housing 26 and non-cylindrical retractor blade handle 60 about the longitudinal axis of the non-cylindrical retractor blade handle 60. The illustrated embodiment is also shown as incorporating a retainer ring 24, which is configured for engagement with a groove 23 located on the proximate end 18 of the sleeve 22, thereby aiding in maintaining the engagement of the sleeve 22 within the clamping bore 14.

In the illustrated embodiment, the locking mechanism 45 is a cam mechanism that engages a through rod 46, bushing 52, and nut 50 to rotatably connect a second clamping member 16 to a first clamping member 12. However, the present invention is capable of incorporating different types of locking mechanisms 45 other the cam mechanism of the illustrated embodiment of the invention, as will be appreciated by those skilled in the art.

As illustrated in FIGS. 3 and 5, the pawl mechanism 30 is pivotably connected to the adapter housing 26 by a fastener 33, such as a screw, bolt, or pin. The pawl mechanism 30 has a wedge 34 and an upper portion 36. A spring pin 32, which is operably connected to the pawl mechanism 30, biases the wedge 34 against at least one adjacent serration 62, thereby providing automatic engagement of the pawl mechanism 30 with the non-cylindrical retractor blade handle 60.

In the illustrated embodiment, as the non-cylindrical retractor blade handle 60 traverses through the adaptor housing 26, the wedge 34 engages and slides across the side of the passing adjacent serration 62. This sliding motion exerts sufficient pressure on the pawl mechanism 30 so as to overcome the biasing force of the spring pin 32. The continuing movement of the non-cylindrical retractor blade handle 60 through the adapter housing 26 creates the continuous automatic disengagement from the passing adjacent serration 62 and subsequent automatic reengagement with the successive serrations 62. Once the non-cylindrical retractor blade handle 60, and attached retractor blade 340, reach the desired location, the linear movement of the non-cylindrical retractor blade handle 60 ceases, and the biasing force of the spring pin 32 automatically forces the pawl mechanism 30 into a locking engagement with at least one of the adjacent serrations 62 that is representative of the linear position of the adapter housing 26 relative to the non-cylindrical retractor blade handle 60.

Similar to a traditional ratchet, when at least one serration 62 is engaged with the pawl mechanism 30, the configuration of the wedge 34 in relation to the shape of the serrations 62, and in conjunction with the biasing force of the spring pin 32, only allows for the linear movement of the non-cylindrical retractor blade handle 60 in one direction through the adapter housing 26. In the illustrated embodiment, this one-way ratchet movement allows the surgeon to draw the head 70 of the non-cylindrical retractor blade handle 60, and attached retractor blade 360, towards the crank universal joint 10 until the retractor blade 340 reaches an optimal position within the incised opening 460 (shown in FIG. 1). Once the linear movement of the crank universal joint 10 ceases, the automatic locking engagement between the pawl mechanism 30 and at least one of the plurality of serrations 62 prevents the retractor blade 340 from being dislodged in a direction away from the crank universal joint 10.

The non-cylindrical retractor blade handle 60 may also be positioned by manually asserting sufficient pressure against the upper portion 36 of the pawl mechanism 30 so as to overcome the biasing force of the spring pin 32. The pawl mechanism 30 then pivots about the fastener 33, thereby releasing the wedge 34 from a locking engagement with at least one of the plurality of serrations 62. The non-cylindrical retractor blade handle 60 may then traverse back and forth through the adaptor housing 26, thereby either drawing the head of the non-cylindrical retractor blade handle 60 or the end cap 68 of the non-cylindrical retractor blade handle 60 towards the adaptor housing 26. When the non-cylindrical retractor blade handle 60 is positioned at the desired location, the pressure against the pawl mechanism 30 may then be released, thereby allowing the biasing force of the spring pin 32 to force the wedge 34 back into locking engagement with at least one of the plurality of serrations 62.

As shown in FIGS. 4 and 5, the illustrated embodiment includes a pinion 27 that assists the surgeon in precisely controlling the linear position of the non-cylindrical retractor blade handle 60 and attached retractor blade 340 shown in FIG. 1. The pinion 27, which is operably connected to the adapter housing 26, has a plurality of teeth 25 that are configured for engagement with at least one of the plurality of serrations 62 along the non-cylindrical retractor blade handle 60. A crank knob 28 may be operably connected to the pinion. The rotation of the crank knob 28 rotates the pinion 27 about the axis of the pinion shaft 29, thereby facilitating the repeated engagement and disengagement of the plurality of teeth 25 with successive serrations 62 and forcing the non-cylindrical retractor blade handle 60 to linearly traverse through retractor handle passageway 38 of the adapter housing 26. However, in the illustrated embodiment, similar to a traditional ratchet, when the pawl mechanism 30 is in a locking engagement with at least one of the plurality of serrations 62, the crank knob 28 and pinion 27 may only rotate in a direction that pulls the head 70 of the non-cylindrical retractor blade handle 60, and attached retractor blade 340, into closer proximity to the proximate end 18 of the adaptor housing 26.

FIG. 4 illustrates a partial cross sectional view of the rear side of the illustrated crank universal joint. In the illustrated embodiment, the distal portion 19 of the adaptor housing 26 may have a dimension larger than the diameter of the clamping bore 14 to prevent the adaptor housing 26 from passing through the clamping bore 14. Alternatively, a retainer ring may be operably attached to both the proximate end 18 and the distal portion 19 of the adapter housing 26 so as to maintain a rotational engagement between the adaptor housing 26 and the clamping bore 14.

In the illustrated embodiment, the first clamping member 12 is operably connected to a second clamping member 16. As shown in FIG. 4, the first clamping member 12 has a first leg 80, a second leg 82, and a bushing orifice 55. The second clamping member 16 is shown as having a passageway 17, a first leg 86, a second leg 88, and a bushing orifice 53. The passageway 17 is configured for engagement with at least a portion of the surgical retractor system frame, such as the extension arms 190, 200. However, the present invention is capable of methods of attachment to a surgical retraction system 100 other than the use of a second clamping member 16, as will be appreciated by those skilled in the art.

In FIGS. 5 and 6 of the illustrated embodiment, the locking mechanism 45 is shown as a cam mechanism having a cam 44 and a cam handle 42 for engagement with a through rod 46 and nut 50, and to operably connect the second clamping member 16 to the first clamping member 12. In the illustrated embodiment, the through rod 46 is configured to permit the independent rotational movement of the first and second clamping members 12, 16 about the longitudinal axis of the through rod 46. Once the first clamping member 12 is placed at its desired location relative to the rotational position of the second clamping member 16, the cam handle 42 is manipulated to a clamping position, thereby locking the rotational positions of the first and second clamping members 12, 16. A bushing 52 may be employed to assist in locking the rotational positions of the first and second clamping members 12, 16. However, the locking of the rotational positions of the first and second clamping members 12, 16 does not prohibit the linear adjustment of the non-cylindrical retractor blade handle 60, which may still be adjusted through the automatic or manual manipulation of the pawl mechanism 30.

In the illustrated embodiment, the cam handle 42 is pivotally moveable about a pivot axis 43 between an unclamped position, as illustrated by solid lines in FIG. 10, and a clamped position, as illustrated by phantom lines in FIG. 10. The cam 44 may be asymmetric with respect to the pivot axis 43 of the cam handle 42, so that the center axis of the cam 44 is not aligned with the pivot axis 43 of the cam handle 42.

The cam 44 is positioned through the eyelet portion 48 of the through rod 46. Alternatively, the center axis of the cam 44 may be aligned with the center axis of the cam handle 42, where the cam 44 is not circular but instead has different radial lengths along different points of its perimeter, as will be appreciated by those skilled in the art.

By way of example, FIG. 7 illustrates the asymmetric position of the center axis of the cam 44 relative to the pivot axis 43 of the cam handle 42. As the cam handle is manipulated from an unclamped position, as shown in FIG. 7, towards a clamped position, as illustrated in FIGS. 8 and 9, the location of the center axis of the cam 44 relative to the pivot axis 43 of the cam handle 42 changes. Once the cam handle 42 reaches the clamped position, the center axis of the cam 44 has, by way of example, rotated to a location below the center axis of the cam 44, as illustrated in FIG. 9. As the cam handle 42 is manipulated from an unclamped position to the clamped position, the cam 44, through contact with the surface of the eyelet portion 48, pulls the through rod 46 and associated nut 50 towards the first clamping member 12. The nut 50 then begins to push the second leg 88 of the second clamping member 16 towards the first clamping member 12. However, in response to the pushing force of the nut 50, the obstructive presence of the bushing 52 forces the bushing 52 into a tight engagement with the bushing orifices 53, 55. In conjunction with the pushing movement of the nut 50, the obstructive presence of the bushing 52 results in the exertion of a compressive force against the second legs 82, 88 of the clamping members, thereby forcing the second legs 82, 88 into closer proximity to their respective first legs 80, 86. The change in the respective proximity of the second legs 82, 88 to first legs 80, 86 results in the constriction of the areas circumscribed by the passageway 17 and the clamping bore 14. Constriction of the clamping bore 14 generates a clamping force onto the sleeve 22, which locks the rotational position of adaptor housing 26 within the clamping bore 14. Furthermore, the compressive forces being exerted by the bushing 52 and the nut 50 onto the first and clamping members 12, 16 locks the rotational positions of the first and second clamping members 12, 16.

FIG. 10 illustrates a side view of the illustrated embodiment of the crank universal joint. In the illustrated embodiment, the non-cylindrical retractor blade handle 60 is permanently integrated into the adaptor housing 26, such that the end cap 68 and retractor head 70 prohibit the removal of the non-cylindrical retractor blade handle 60 from the adaptor housing 26. In an attempt to reduce and/or eliminate possible interference with the operative site, the locking mechanism may be configured so that the cam handle 42 extends towards the operative site only when the cam handle 42 is in an unclamped position, as depicted by solid lines in FIG. 10. When the cam handle is in the clamped position, as depicted by the phantom lines in FIG. 10, the cam handle 42 extends away from the operative site. Furthermore, the locking mechanism 45 may be configured so that the unclamped and clamped positions of the cam handle 42 are substantially parallel to the longitudinal axis of the non-cylindrical retractor blade handle 60 so as to further prevent the cam handle from interfering with the operative site.

While the present invention has been illustrated in some detail according to the preferred embodiment shown in the foregoing drawings and descriptions, it will be understood that the invention is not limited thereto, since modifications may be made by those skilled in the art, particularly in light of the foregoing teaching. It is therefore contemplated by the appended claims to cover such modifications as incorporate those features that come within the spirit and scope of the invention.

What is claimed is:

1. A universal clamping joint comprising:
   a first clamping member having a clamping bore;
   a non-cylindrical retractor blade handle, the non-cylindrical retractor blade handle having a plurality of serrations;
   an adapter housing having a retractor handle passageway and a sleeve, at least a portion of the sleeve being configured for rotational insertion into the clamping bore, at least a portion of the retractor handle passageway having a non-cylindrical configuration sized to receive the slideable insertion of the non-cylindrical retractor blade handle and to prevent the rotation of the non-cylindrical retractor blade handle within the adapter housing;
   a pinion operably connected to the adaptor housing, the pinion having a plurality of pinion teeth, the pinion teeth being configured for engagement with at least one of the plurality of serrations;
   a locking mechanism operably connected to the first clamping member, the locking mechanism being movable between an unclamped position and a clamped position, the clamped position being capable of imposing a clamping force on the clamping bore to prevent the rotation of the adaptor housing within the clamping bore; and
   a pawl mechanism operably connected to the adaptor housing, the pawl mechanism being configured for both a releasable engagement and a locking engagement with at least one of the plurality of serrations.

2. A universal clamping joint comprising:
   a first clamping member having a clamping bore;
   a non-cylindrical retractor blade handle, the non-cylindrical retractor blade handle having a plurality of serrations;
   an adapter housing having a retractor handle passageway and a sleeve, at least a portion of the sleeve being configured for rotational insertion into the clamping bore, at least a portion of the retractor handle passageway having a non-cylindrical configuration sized to receive the slideable insertion of the non-cylindrical retractor blade handle and to prevent the rotation of the non-cylindrical retractor blade handle within the adapter housing;
   a pinion operably connected to the adaptor housing, the pinion having a plurality of pinion teeth, the pinion teeth being configured for engagement with at least one of the plurality of serrations;
   a crank knob operably connected to the pinion, the rotation of the crank knob facilitating the rotation of the plurality of pinion teeth and subsequent engagement of at least one of the plurality of pinion teeth with at least one of the plurality of serrations;
   a locking mechanism operably connected to the first clamping member, the locking mechanism being movable between an unclamped position and a clamped position, the clamped position being capable of imposing a clamping force on the clamping bore to prevent the rotation of the adaptor housing within the clamping bore; and
   a pawl mechanism operably connected to the adaptor housing, the pawl mechanism being configured for both a releasable engagement and a locking engagement with at least one of the plurality of serrations.

3. The apparatus of claim 1 or 2 wherein a spring pin is operably connected to the pawl mechanism, the spring pin being configured to bias the pawl mechanism against at least one of the plurality of serrations.

4. The apparatus of claim 1 or 2 wherein at least a portion of the retractor handle passageway is a cylindrical orifice.

5. The apparatus of claim 1 or 2 wherein the locking mechanism is a cam locking mechanism, the cam locking mechanism having a cam handle and a cam.

6. The apparatus of claim 5 wherein the locking mechanism engages a through rod and a nut.

7. The apparatus of claim 5 wherein the cam handle has an unclamped position and a clamping position, the unclamped position and the unclamped position of the cam handle being configured to be substantially parallel to the non-cylindrical retractor blade handle.

8. The apparatus of claim 1 or 2 wherein a second clamping member is rotatably connected to the first clamping member, the second clamping member and the first clamping member being capable of rotational movement about the same axis.

* * * * *